United States Patent [19]

Sundby

[11] 4,056,558

[45] * Nov. 1, 1977

[54] SULFOSUCCINATES OF POLYHYDROXY TERTIARY AMINES AS NEW DETERGENT-SOFTENER COMPOUNDS

[75] Inventor: Bjorn Sundby, Halifax, Canada

[73] Assignee: Colgate-Palmolive Company, New York, N.Y.

[*] Notice: The portion of the term of this patent subsequent to Dec. 23, 1992, has been disclaimed.

[21] Appl. No.: 424,250

[22] Filed: Dec. 12, 1973

Related U.S. Application Data

[63] Continuation-in-part of Ser. No. 205,395, Dec. 6, 1971, Pat. No. 3,928,422.

[51] Int. Cl.$^2$ .................................. C07C 143/15
[52] U.S. Cl. .................................. 560/151; 252/354; 252/526; 252/545
[58] Field of Search ............... 252/354, 526; 260/481 R

[56] References Cited

U.S. PATENT DOCUMENTS

| | | | |
|---|---|---|---|
| 2,176,423 | 10/1959 | Jaeger | 260/481 |
| 2,844,608 | 7/1958 | Hagge et al. | 260/481 R |
| 3,002,995 | 10/1961 | Williams | 260/481 |
| 3,080,280 | 3/1963 | Lindner | 260/481 R |
| 3,349,122 | 10/1967 | Segesseman | 260/513 B |

FOREIGN PATENT DOCUMENTS 1,487,622  5/1967  France .............................. 260/485 G

OTHER PUBLICATIONS

Chem. Abstracts, 47:6181e.

Primary Examiner—Vivian Garner
Attorney, Agent, or Firm—Herbert S. Sylvester; Murray M. Grill; Norman Blumenkopf

[57] ABSTRACT

Novel sulfosuccinates of 2-hydroxy alkyl tertiary alcohol amines having the structural formula:

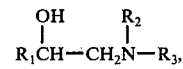

wherein $R_1$ is a monovalent aliphatic hydrocarbon radical of 8 to 24, preferably 10 to 20 carbon atoms; $R_2$ is an alkyl or alkylol (hydroxy substituted alkyl) radical containing 1 to 6 carbon atoms, and $R_3$ is an alkylol radical containing 1 to 6 carbon atoms, and salts thereof. The reaction mixture consists of sulfonated mono-, di-, and-/or tri-esters, depending on the number of reactive hydroxyl groups in the alcoholamine and the amount of dicarboxylic acid utilized. These novel esters and salts thereof uniquely possess both detergency and softening properties.

12 Claims, No Drawings

SULFOSUCCINATES OF POLYHYDROXY TERTIARY AMINES AS NEW DETERGENT-SOFTENER COMPOUNDS

This application is a continuation-in-part of my co-pending application Ser. No. 205,395, filed on Dec. 6, 1971, now U.S. Pat. No. 3,928,422.

This invention relates to novel sulfosuccinates of 2-hydroxy alkyl tertiary alcohol-amines and salts thereof. It has been discovered that said compounds are useful surface active agents and are substantive to a variety of fibrous materials. Thus, they may be used as emulsifiers, solubilizing agents for lipophilic materials, wetting agents, detergents and softeners for textiles and hair.

Since the introduction of commercial synthetic organic detergents and emulsifiers to replace the conventional watersoluble higher fatty acid soaps, much research work has been performed in an effort to improve such compounds and compositions including them, with the object of obtaining better and more convenient laundering of textiles. As a result, a wide variety of types of surface active agents and detergents have been produced and many such compositions have been manufactured commercially and have been introduced to the market place. As better products were made, the goals set for researchers on detergency were increased and the properties of the desired products were such as to have been thought impossible of attainment only a few years before. Although the cleaning function of surface active materials is still very important and products which clean better than competitive compounds are always in demand, additional attribution of cleaning compounds were desired. For example, with the increasing importance of cold water washing, detergent compositions were desired which would be capable of successfully cleaning and whitening textiles and laundry in cold water, as well as in hot water. Such washing capability is of importance in making a product acceptable for the washing of wool and other shrink-sensitive materials. In addition, softening agents have been found to be a desirable and, in some instances, a necessary ingredient in the washing of textiles. However, because of the imcompatibility of softeners and detergents, it has been necessary to utilize the textile softener in the final rinse as a separate step in a washing cycle. The objections to this procedure are obvious; one must be present during the washing cycle and few washing machines include devices for the addition of softeners in the final rinse.

Therefore, it has been the long desire of the detergent industry to provide a single compound possessing the foaming and detergency characteristics of conventional detergents, yet uniquely possessing fabric softening ability. Such a single compound uniquely possessing both detergency and fabric softening ability would, of course, eliminate the disadvantages of employing two separate materials, and, in addition, would completely eliminate the disadvantages associated with the incompatibility of conventional anionic detergents and cationic fabric softeners.

The sulfonated esters of the instant invention possess detergency, wetting, foaming, and emulsifying properties in both hard and soft waters and at both elevated and lower temperatures. In addition, these compounds exhibit substantivity to materials such as cotton, hair, etc. and are excellent in textile softening activity. This high degree of substantivity is unexpected in a surface active material which itself functions to release adsorbed and absorbed substances from materials being washed. Consequently, instant surface active agents simultaneously clean and soften textiles.

In accordance with the present invention, there are provided novel esters of sulfonated dicarboxylic acids and 2-hydroxyalkyl tertiary alcohol amines and salts thereof consisting predominantly of the mono-ester having the formula:

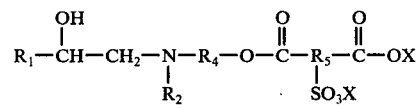

which are effective detergents and which also serve to soften fibrous materials when applied to them, as in aqueous solution. In the formula, $R_1$ is a monovalent aliphatic hydrocarbon radical of 8 to 24 and preferably 10 to 20 carbon atoms (i.e. alkyl), $R_2$ is an alkyl or alkylol (hydroxy substituted alkyl) radical of 1 to 6 carbon atoms, $R_4$ is a divalent aliphatic hydrocarbon radical (i.e., alkylene) of 1 to 6 carbon atoms ($R_4$—OH=$R_3$); $R_5$ is a divalent hydrocarbon radical (i.e., ethylene or $C_{1-6}$ alkyl substituted ethylene) residue of the sulfonated dicarboxylic acid, X is hydrogen or a salt-forming element or radical. If X is an element, it is preferred that it should be an alkali metal such as potassium, sodium and lithium or other suitable salt-forming metal. If X is a radical, it is preferred that such be ammonium, alkylamine or alkanolamine, either mono-, di-, or tri-alkylamine or mono-, di- or tri-alkanolamine, in which the alkyl and alkanol groups of the salt-forming amines are of 1 to 4 carbon atoms, preferably 2 to 3 carbon atoms.

The novel sulfonated esters of the present invention can be prepared by a two-step synthesis comprising the esterification of the polyhydroxy tertiary amine with an unsaturated dicarboxylic acid (i.e., maleic, itaconic, fumaric, citraconic and the like) and subsequently sulfonating the ester with an alkali metal sulfite salt or by other suitable sulfonating means. More specifically, the ester may be formed by reacting the unsaturated dicarboxylic acid or preferably the anhydride thereof with a polyhydroxy tertiary amine having the structure:

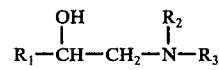

wherein $R_1$ is a monovalent aliphatic hydrocarbon radical of 8 to 24 and preferably 10 to 20 carbon atoms, $R_2$ is an alkyl or hydroxyalkyl radical containing 1 to 6 carbon atoms, $R_3$ is a hydroxy alkyl radical containing 1 to 6 carbon atoms. Examples of

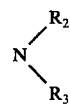

radicals of this class are:

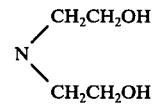

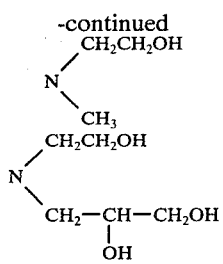

and related compounds in which the radicals contain more carbon atoms than in the formula shown above, e.g., radicals of di(isopropanol)amine, N-methyl-N-isopropanol-amine, N-ethyl-N-ethanolamine, N-ethyl-N-isopropanolamine, N-propyl-N-ethanol-amine, N-propyl-N-isopropanolamine, N-methyl-N-hydroxyethoxyethyl-amine, N-butyl-N-hydroxy-ethoxyethylamine, N-cyclohexyl-N-hydroxyethoxyethylamine, N-butyl-N-ethanolamine, di(hydroxyethoxyethyl)amine, N-hydroxyethoxy-ethoxyethyl-N-methylamine, N-hydroxyethyl-N-hydroxy-isopropylamine, N-benzyl-N-hydroxyethylamine, or N-cyclo-hexyl-N-2-hydroxy-2-phenylethylamine.

The polyhydroxy tertiary amines are known compounds which may be prepared by condensing secondary alcoholamines with long chain epoxides. A typical example of an amine/epoxide reaction is the preparation of 2-hydroxyalkyl-diethanolamine.

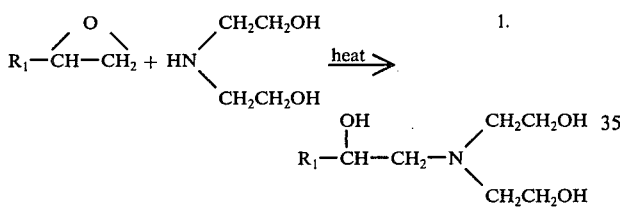

The unsaturated dicarboxylic acid anhydride may be maleic anhydride or a unsubstituted maleic anhydride.

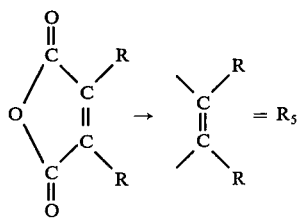

The reaction is predominantly in accordance with the following equations:

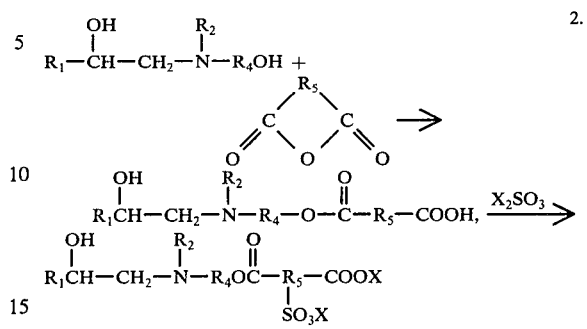

wherein the R radicals are as aforedefined and equimolar amounts of reactants are used. The sulfonation step adds the sulfonate group to the unsaturated acid radical at the point of unsaturation as illustrated by the following equations when utilizing maleic anhydride.

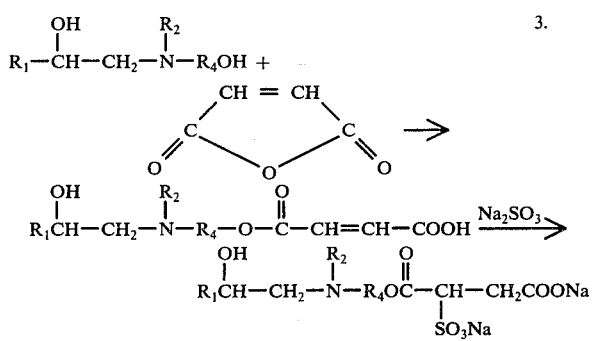

The alcoholamine has at least two hydroxyl groups, one in the long chain resulting from the epoxide ring opening and one or more from the original alcoholamine. When utilizing equimolar amounts of reactants, the primary hydroxyl is preferentially esterified into the mono-ester, since it is the least stearically hindered and therefore the most reactive group. However, when more than one mole of the acid anhydride is used, the other hydroxyl radicals react to form the di-ester, tri-ester, etc. and mixtures thereof. Similarly, the number of hydroxyl groups in the alcoholamine is determinative of the formation of the mono-, di-, or tri-esters.

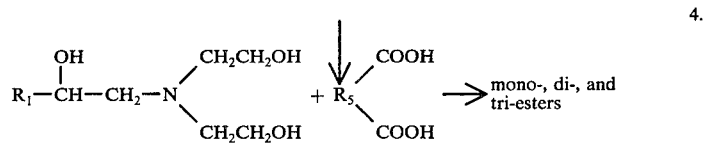

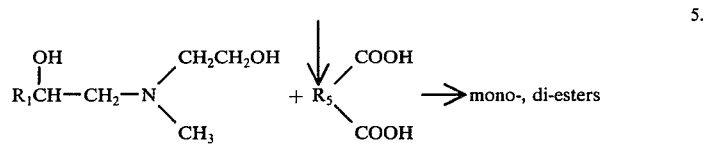

-continued

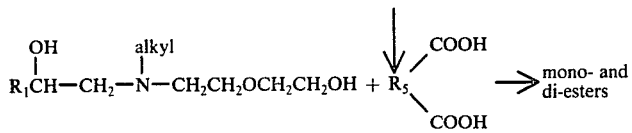
6.

The sulfonated esters formed in accordance with instant invention have one free carboxyl group and one sulfonate group for every esterified carboxyl radical as shown by the following structural formulae:

Mono-ester:
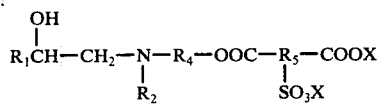

Di-ester:
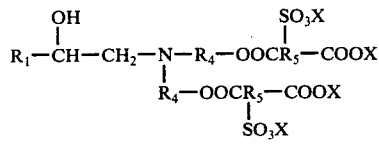

Tri-ester:
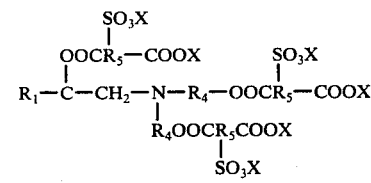

The esterification of the 2-hydroxyalkylalcoholamines with the unsaturated dicarboxylic acid anhydride is an exothermic reaction which can be carried out in aprotic solvent, ether, chloroform or acetone, but it can also be carried out neat. The latter method is preferable as an industrial process, since no solvent is involved, thereby not giving any by-products. The powdered acid anhydride (e.g., maleic anhydride) is added gradually to the liquid alcoholamine which is held at a temperature of about 100° C. When the reaction is over, the product is cooled and subsequently sulfonated by the addition of the ester to an aqueous solution of a sulfite salt. The mixture is heated to about 50°–90° C with agitation, for a period of about 30–60 minutes. A clear, viscous solution is obtained. The final product may be freeze dried and is obtained in the form of a solid, which is insoluble in acetone, ether, etc., but very soluble in water. When utilizng a solvent during the esterification step, the reactants are first dissolved therein and the solution refluxed until the reaction is complete. Evaporation of the solvent yields a resin-like, waxy product, insoluble in water, which is subsequently sulfonated as above. When utilizing the unsaturated dicarboxylic acid in lieu of the anhydride, esterification is controlled so that only one mole of water is removed per mole of alcohol. Termination of esterification at this point ensures the formation of mono-, di-, and/or tri-esters as disclosed in copending application Ser. No. 205,408 filed on Dec. 6, 1971 (replaced by continuation application Ser. No. 409,027 filed Oct. 24, 1973 and now U.S. Pat. No. 3,927,073), and prevents the production of a polymeric linear ester.

The esterification may be controlled by conventional methods of cooling or by other suitable means.

The products obtained are usually clear, viscous solutions of sulfonated mono-, di-, tri-esters and mixtures thereof, readily soluble in water. The sulfonated mono-, di- and tri-esters can be readily separated and purified by chromatographic techniques in the usual manner. However, separation is not necessary. The mixture of mono-, di-, and/or tri-esters can be used as the effective detergent, due to their combined property of detergency and fabric conditioning (softening, anti-static, etc.). The high viscosity solutions that some members of this series form render them particulary useful in shampoos.

Examples of sulfonated esters in accordance with the present invention include:

Sulfosuccinate of N-(2-hydroxy hexadecyl) diethanolamine

Sulfosuccinate of N-(2-hydroxy octadecyl) diethanolamine

Sulfosuccinate of N-(2-hydroxy octadecyl) diisopropanol-amine

Sulfosuccinate of N-(2-hydroxy octadecyl) diglycolamine

Sulfosuccinate of N-(2-hydroxy octadecyl) methylethanolamine

Sulfosuccinate of N-(2-hydroxy dodecyl) diethanolamine

Sulfosuccinate of N-(2-hydroxy dodecyl) diisopropanolamine

Sulfosuccinate of N-(2-hydroxy dodecyl) diglycolamine

Sulfosuccinate of N-(2-hydroxy dodecyl) methylethanolamine

Sulfosuccinate of N-(2-hydroxy tetradecyl) diethanolamine.

The novel sulfonated esters of the present invention, in addition to possessing excellent detergency and fabric softening properties, have been found to be compatible with the various detergent builders and other additives conventionally employed in detergent compositions. Accordingly, it is possible to formulate a detergent composition based upon the sulfonated esters of instant invention as the sole detergent and fabric softener.

Various embodiments of the present invention will now be illustrated by reference to the following specific examples. It is to be understood, however, that such examples are presented for purposes of illustration only and the present invention is in no way to be deemed as limited thereby.

EXAMPLE 1

Preparation of disodium sulfosuccinate of N-(2-hydroxyhexadecyl) diethanolamine:

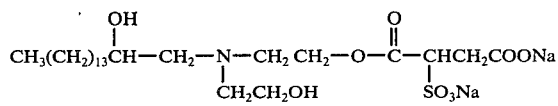

10 gms. maleic anhydride was stirred into a hot melt (100° C) of 35 gm. 2-hydroxyhexadecyldiethanolamine. The mixture became rapidly very viscous. After 10 minutes, it was cooled and added to 12 gms. sodium sulfite in 100 ml water. The mixture was heated to 90° C with stirring. After one hour, a clear viscous solution was obtained. The product was freeze dried, yielding a solid, which is insoluble in acetone, ether, etc., but very soluble in water. This sulfosuccinate produces a very dense foam in aqueous solution.

EXAMPLE 2

Preparation of disodium sulfosuccinate of N-(2-hydroxy octadecyl) methylethanolamine:

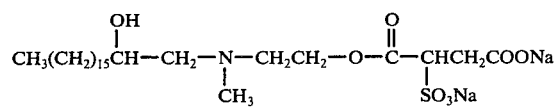

This product is prepared as in Example 1.

EXAMPLE 3

Preparation of disodium sulfosucinate of n-(2-hydroxy octadecyl) diisopropanolamine:

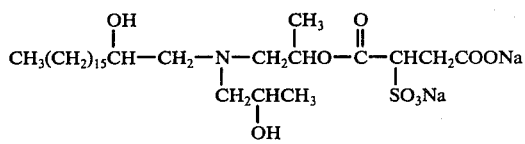

This produce is prepared as in Example 1.

EXAMPLE 4

Preparation of tetrasodium disulfosuccinate of N-(2-hydroxy-octadecyl) methylethanolamine:

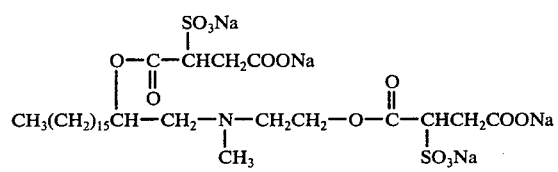

This product is prepared as in Example 1, except that 20 gms. maleic anhydride and 24 gms. sodium sulfite in 200 ml. water are used.

EXAMPLE 5

Preparation of hexasodium trisulfosuccinate of N-(2-hydroxy-hexadecyl) diethanolamine:

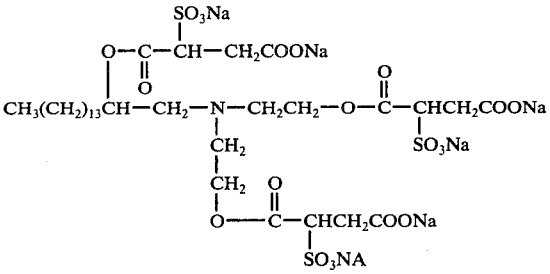

This product is prepared as in Example 1, except that 30 gms. maleic anhydride and 36 gms. sodium sulfite in 300 ml. water are used.

The instant novel sulfonated esters and salts thereof were tested for their detergency properties as well as their efficacy as fabric softeners. The Spangler soil detergency tests were run using an aqueous solution containing 1.5 g. of detergent/liter water (0.15% product concentration) said detergent comprising 15% of the compound to be tested, 35% sodium tripolyphosphate and 50% sodium sulfate (based on dry ingredients), in soft and hard water, at both 70° F. and 120° F. Three Spangler soil swatches were washed 10 minutes in a Tergotometer at 100 rpm, rinsed 5 minutes, and dried. The ingredients were dry-blended by conventional methods and added to the aqueous system in the Tergotometer.

TABLE I

| | | Rd (Soil Removal) | | |
| --- | --- | --- | --- | --- |
| | | 70° F | | 120° F |
| Compound | | NB-TAP | 300 PPM | NB-TAP | 300 PPM |
| 1. Disodium sulfosuccinate of N-(2-hydroxyhexadecyl) diethanolamine | | 12.3 | 11.2 | 17.6 | 12.5 |
| 2. Control-linear tridecyl benzene sulfonate | | 16.2 | 9.9 | 21.0 | 12.2 |
| 3. Disodiumsulfosuccinate of N-(2-OHC$_{18}$) diethanolamine | | 12.8 | 10.2 | 17.1 | 13.5 |
| 4. Disodium sulfosuccinate of N-(2-OHC$_{18}$) methyl ethanolamine | | 14.3 | 10.9 | 13.6 | 13.0 |
| 5. Disodium sulfosuccinate of N(2-OHC$_{18}$) diisopropanolamine | | 14.4 | 11.2 | 13.9 | 16.3 |

Similarly, the test for softening effect on cotton materials is run by washing one terry cloth towel in 17 gallons of NB tap water at 120° F and air drying. The softness is rated on the scale of 1 to 10, with 1 indicating no softness, and 10 representing maximum softness.

TABLE II

| | Softness Ratings |
| --- | --- |
| 1. 10 g AI sulfosuccinate of N-(2-hydroxy-hexadecyl) diethanolamine, 40g Pentasodium Tripolyphosphate (NaTPP) | 7 |
| 2. 10% sulfosuccinate of N-(2-hydroxy-octadecyl) methylethanolamine - 40% NaTPP | 10 |
| 3. 10% sulfosuccinate of N-(2-hydroxy-octadecyl) diisopropanolamine - 40% NaTPP | 10 |
| 4. 5g AI sodium sulfosuccinate in (1), 10g AI linear dodecyl benzene sulfonate, 40 g NaTPP | 5 |
| 5. 30g sulfosuccinate of N-(2-hydroxy-octadecyl) diethanolamine | 10 |
| 6. Linear tridecyl benzene sulfonate | 1 |

The results shown above indicate an unexpectedly excellent detergency in hard and soft water, both cold and hot, as compared to commercial detergent linear tridecyl benzene sulfonate. In addition to possessing excellent detersive properties, instant sulfonated esters exhibit excellent fabric softening characteristics, not possessed by the control. Similar results are obtained with other sulfonated esters of 2-hydroxy alkyl tertiary alcohol-amines.

The present invention has been described in conjunction with various illustrations and embodiments thereof set forth in the specification. However, it is evident that equivalents may be substituted for the present compounds and procedural steps, without departing from the principles of this invention or the spirit thereof. Those of skill in the art will recognize what equivalents and substitutes are also within the scope of the present disclosure.

I claim:

1. Sulfosuccinate esters of the formula:

$$\begin{array}{cc} A & R_2 \\ | & | \\ R_1-CH-CH_2-N-R_3 \end{array}$$

wherein
$R_1$ is $C_{8-24}$ alkyl;
A is OH or

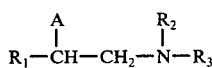

$R_2$ is $C_{1-6}$ alkyl or hydroxyalkyl or

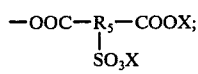

$R_3$ is $C_{1-6}$ hydroxyalkyl or

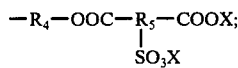

$R_4$ is $C_{1-6}$ alkylene;
$R_5$ is ethylene or $C_{1-6}$ alkyl-substituted ethylene;
X is H or a salt-forming member of the group consisting of alkali metal, ammonium, mono, di-and tri-$C_{1-4}$ alkylamine, and mono-, di- and tri-$C_{1-4}$ alkanolamine;
and at least one of $R_2$ and $R_3$ is

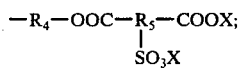

or mixtures of mono-, di- and tri-esters having said formula.

2. A sulfosuccinate di-ester according to claim 1 in which A is

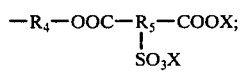

$R_2$ is methyl, $R_3$ is

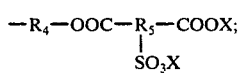

and $R_4$ and $R_5$ are each ethylene.

3. A sulfosuccinate tri-ester according to claim 1 in which A is

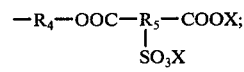

$R_2$ and $R_3$ are each

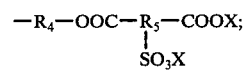

and $R_4$ and $R_5$ are each ethylene.

4. A mixture of sulfosuccinate esters according to claim 1 containing
 1. mono-esters in which A is OH, $R_2$ is $C_{1-6}$ alkyl or hydroxyalkyl, and $R_3$ is

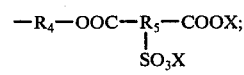

2. di-esters in which A is OH and $R_2$ and $R_3$ are each

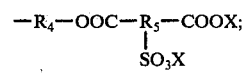

or in which A is

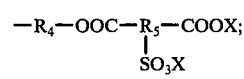

$R_2$ is $C_{1-6}$ alkyl or hydroxyalkyl and $R_3$ is

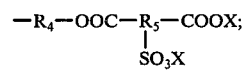

and
 3. tri-esters in which A is

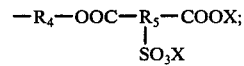

and $R_2$ and $R_3$ are each

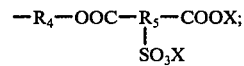

5. Sulfosuccinate esters according to claim 1 in which $R_5$ is ethylene.

6. Sulfosuccinate esters according to claim 5 in which X is sodium.

7. Sulfosuccinate esters of the formula

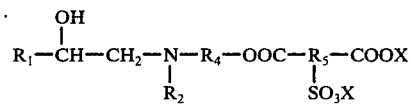

wherein
- $R_1$ is $C_{8-24}$ alkyl;
- $R_2$ is $C_{1-6}$ alkyl or hydroxalkyl;
- $R_4$ is $C_{1-6}$ alkylene;
- $R_5$ is ethylene or $C_{1-6}$ alkyl-substituted ethylene; and X is H or a salt-forming member of the group consisting of alkali metal, ammonium, mono-, di-and tri-$C_{1-4}$ alkyl amine and mono-, di-and tri-$C_{1-4}$ alkanolamine.

8. A sulfosuccinate mono-ester according to claim 7 in which $R_2$ is hydroxyethyl, and $R_4$ and $R_5$ are each ethylene.

9. A sulfosuccinate mono-ester according to claim 7 in which $R_2$ methyl and $R_4$ and $R_5$ are each ethylene.

10. A sulfosuccinate mono-ester according to claim 7 in which $R_2$ is 2-hydroxypropyl, $R_4$ is isopropylene, and $R_5$ is ethylene.

11. Sulfosuccinate esters according to claim 7 in which $R_5$ is ethylene.

12. Sulfosuccinate esters according to claim 11 in which X is sodium.